United States Patent [19]
Grauert et al.

[11] Patent Number: 5,945,535
[45] Date of Patent: Aug. 31, 1999

[54] METHOD OF PREPARING NORBENZOMORPHANES

[75] Inventors: Matthias Grauert; Herbert Merz, both of Ingelheim; Hanfried Baltes, Wöllstein, all of Germany

[73] Assignee: Boehringer Ingelheim KG, Ingelheim, Germany

[21] Appl. No.: 08/982,000

[22] PCT Filed: Aug. 2, 1996

[86] PCT No.: PCT/EP96/03401

§ 371 Date: May 1, 1998

§ 102(e) Date: May 1, 1998

[87] PCT Pub. No.: WO97/06146

PCT Pub. Date: Feb. 20, 1997

[30] Foreign Application Priority Data

Aug. 3, 1995 [DE] Germany .............. 195 28 472

[51] Int. Cl.[6] ............................... C07D 221/12
[52] U.S. Cl. ............................... 546/97; 546/242
[58] Field of Search .................. 546/97

[56] References Cited

U.S. PATENT DOCUMENTS

| | | | |
|---|---|---|---|
| 4,012,392 | 3/1997 | Akkermann et al. | 546/97 |
| 4,293,556 | 10/1981 | Merz et al. | 546/97 |
| 4,406,904 | 9/1983 | Welle et al. | 546/97 |
| 5,607,941 | 3/1997 | Merz et al. | 514/289 |
| 5,731,318 | 3/1998 | Carter et al. | 546/97 |

FOREIGN PATENT DOCUMENTS

| | | |
|---|---|---|
| 0 028 717 | 5/1981 | European Pat. Off. . |
| 0 521 422 A1 | 1/1993 | European Pat. Off. . |
| 2 027 077 | 12/1970 | Germany . |

*Primary Examiner*—Donald G. Daus
*Attorney, Agent, or Firm*—Robert P. Raymond; Alan R. Stempel; Mary-Ellen Devlin

[57] ABSTRACT

The present invention relates to a new process for preparing norbenzomorphan, the central intermediate step in the preparation of pharmaceutically useful benzomorphan derivatives of general formula 1

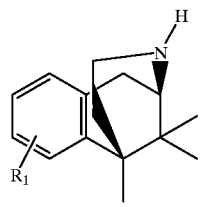

especially (−)-(1R,5S,2"R)-3'-hydroxy-2-(2-methoxypropyl)-5,9,9-trimethyl-6,7-benzomorphan or [(−)-(2R,6S,2'R)-3-(2-methoxypropyl)-6,11,11-trimethyl-1,2,3,4,5,6-hexahydro-2,6-methano-benzo[α]oxacin-9-ol] (BIII 277).

6 Claims, No Drawings

METHOD OF PREPARING NORBENZOMORPHANES

The present invention relates to a new process for preparing norbenzomorphan—the central intermediate in the preparation of pharmaceutically useful benzomorphan derivatives of general formula 1, particularly (−)-(1R,5S, 2"R)-3'-hydroxy-2-(2-methoxypropyl) -5,9,9-trimethyl-6,7-benzomorphan and [(−)-(2R,6S,2'R)-3-(2-methoxypropyl)-6,11,11-trimethyl-1,2,3,4,5,6-hexahydro-2,6-methano-benzo[α]oxacin-9-ol] (BIII 277).

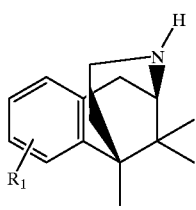

1 wherein
$R_1$ denotes hydrogen, $C_{1-6}$-alkyl, halogen, hydroxy, $C_{1-8}$-alkoxy, a benzoyl group bound via an oxygen or an alkylcarboxyl group having a straight-chained or branched $C_{1-6}$-lower alkyl group—wherein the alkyl group may optionally be substituted by one or more halogen atoms which may be identical or different
nitro, cyano, $NH_2$, $NH(C_{1-8}$-alkyl), $N(C_{1-8}$-alkyl)$_2$, wherein the alkyl groups may be identical or different, NH-acyl-($C_{1-8}$-alkyl), wherein acyl denotes benzoyl or an alkylcarbonyl group having a straight-chained or branched $C_{1-6}$-lower alkyl group, whilst the alkyl group may optionally be substituted by one or more halogen atoms which may be the same as one another or different from one another.

Unless otherwise specifically stated, the general definitions are used as follows:

$C_{1-6}$-alkyl or $C_{1-8}$-alkyl generally denotes a branched or unbranched hydrocarbon group having 1 to 6 or 1 to 8 carbon atoms, which may optionally be substituted by one or more halogen atoms, preferably fluorine, which may be the same as or different from one another. The following hydrocarbon groups are mentioned by way of example: methyl, ethyl, propyl, 1-methylethyl (isopropyl), butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylproypyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless otherwise stated, lower alkyl groups having 1 to 3 carbon atoms such as methyl, ethyl, propyl and isopropyl are preferred.

Acyl generally denotes benzoyl or alkylcarbonyl groups—such as straight-chained or branched lower alkyl having 1 to about 6 carbon atoms, which are bound via a carbonyl group, the alkyl group optionally being substituted by one or more halogen atoms which may be the same as or different from one another. Alkyl groups having up to 4 carbon atoms are preferred. Examples include: acetyl, trifluoroacetyl, ethylcarbonyl, propylcarbonyl, isopropylcarbonyl, butylcarbonyl and isobutylcarbonyl. The acetyl group is particularly preferred.

The benzomorphan derivatives mentioned hereinbefore constitute highly promising active substances for treating neurodegenerative disorders as well as cerebroischaemias of various origins. The following may be mentioned by way of example: status epilepticus, hypoglycaemia, hypoxia, anoxia, cerebral trauma, cerebral oedema, amorphous lateral sclerosis, Huntington's disease, Alzheimer's disease, hypotonia, cardiac infarct, cerebral stroke and perinatal asphyxia. The benzomorphan derivative numbered BIII 277 and related benzomorphans are described in detail in German Offenlegungsschrift DE-OS 41 21 821, inter alia.

In addition, other methods of synthesis for producing benzomorphan derivatives are known from the prior art [German Offenlegungsschrift 2 027 077, published European Application 0 004 960]. However, with the exception of DE-OS 41 21 821, these publications merely describe methods of synthesising the racemates, which have to be cleaved and eventually 50% of unwanted isomer have to be discarded. Furthermore, in some reaction steps, there is the risk of the formation of regioisomers.

The objective of the present invention is therefore to overcome the disadvantages of the processes known from the prior art and to provide a method of production which on the one hand avoids the formation of any regioisomers during the synthesis of the basic benzomorphan structure and on the other hand makes it possible to obtain the pharmacologically active stereoisomer in higher yields.

This objective is achieved by the process described below and, more particularly, by the process steps described in the Examples. Various other, additional features, embodiments of the process and the like associated with the invention will become apparent to those skilled in the art from the description which follows and will be more readily understood in conjunction with the Examples, which illustrate the currently preferred embodiments of the present invention by way of example. However, it is expressly pointed out that the Examples and the associated description are provided purely for the purposes of illustration and description and are not to be regarded as restricting the invention, particularly to the preparation of (−)-(2R,6S,2'R)-3-(2-methoxypropyl)-6,11,11-trimethyl-1,2,3,4,5,6-hexahydro-2, 6-methano-benzo [α]oxacin-9-ol (BIII 277).

In contrast to the processes known from the prior art, the present invention proposes an improved method of manufacture in which, in the first step, a suitably substituted benzylcyanide derivative (2)—m-methoxybenzylcyanide, for example, in the preparation of BIII 277—is reacted with ethylbromoisobutyrate (3) to obtain the correspondingly substituted ethyl 3-amino-2,2-dimethylbutanoate derivative (4)—ethyl 3-amino-4-(3-methoxyphenyl)-2,2-dimethylbutanoate in the manufacture of BIII 277—:

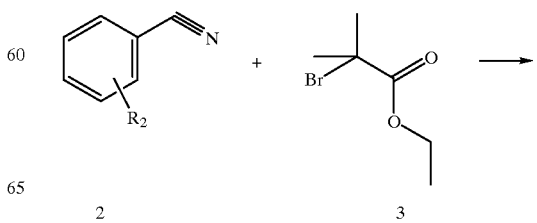

2                                  3

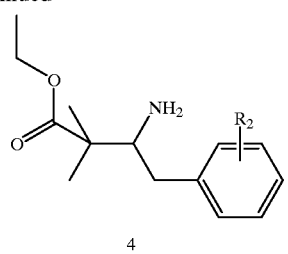

4

Thus, the process proposed according to the invention makes it possible to synthesise the 3-aminodimethylbutanoic acid precursor known from DE OS 20 27 077 in one reaction step, starting from cheap starting materials, whereas the prior art specified requires 4 steps.

In order to carry out this reaction, which is a type of Reformatsky reaction, an alkylhalosilane, preferably a trialkylchlorosilane, most preferably trimethylchlorosilane, and zinc powder are placed in a solvent which is inert under the reaction conditions chosen, preferably an ether or in a halohydrocarbon, most preferably dichloromethane. After the mixture has been diluted with an inert polar solvent, preferably a cyclic ether, most preferably tetrahydrofuran, the reaction mixture is heated, preferably to reflux temperature, and mixed with a mixture of the ethylbromoisobutyrate (3) and the suitably substituted benzylcyanide (2) and heated further, preferably to reflux temperature. After the reaction mixture has been cooled and the zinc powder has been filtered off, the mixture is combined with a reducing agent which is selective in terms of the reduction of imino functions, preferably a complex alkali metal borohydride derivative, most preferably sodium cyanoborohydride, and then with an alkanol, preferably a straight-chained or branched $C_{1-4}$-alcohol, most preferably ethanol. Then an aqueous solution of a basically reacting compound, preferably ammonia solution, most preferably concentrated ammonia solution, is added and the organic phase of the reaction mixture is isolated. After drying and evaporation in vacuo the residue remaining is taken up in an inert solvent, preferably in an aliphatic or aromatic hydrocarbon, most preferably in toluene, and extracted with an aqueous solution of an acid, preferably an inorganic acid, most preferably 2 N hydrochloric acid. Finally, the aqueous phase is made alkaline with an aqueous solution of a basically reacting compound, preferably ammonia solution, most preferably concentrated ammonia solution, and then extracted with an organic, water-immiscible extracting agent, preferably a halohydrocarbon, most preferably dichloromethane. The extract thus obtained is dried and evaporated down and the ethyl 3-amino-2,2-dimethylbutanoate derivative (4) is isolated.

It has now been found, surprisingly, that at this stage of the reaction the C—C coupling reaction and reduction of the imino group to the amine can be carried out in a single step, without first having to isolate and purify the imine, as is necessary in catalytic hydrogenation. This will avoid the formation of hydrolysis products, the occurrence of which leads to a reduction in yield during conventional aqueous working up.

In the second stage of the reaction, the ethyl 3-amino-2,2-dimethylbutanoate derivative 4 is reacted with ethyl acrylate to obtain the corresponding ethyl 3-(2-ethoxycarbonylethyl)amino-2,2-dimethylbutanoate derivative 5—which in the case of the preparation of BIII 277 might be, for example: ethyl 3-(2-ethoxycarbonylethyl)amino-4-(3-methoxyphenyl)-2,2-dimethylbutanoate ($R_2$=$CH_3O$):

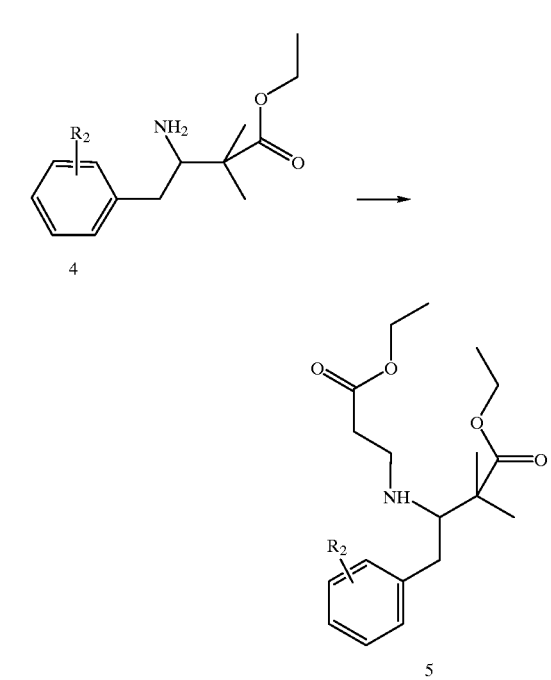

In order to carry out this Michael addition, the ethyl 3-amino-2,2-dimethylbutanoate derivative 4 is dissolved with ethyl acrylate in a reaction medium which is inert under the reaction conditions chosen, preferably in a straight-chained or branched $C_{1-4}$-alkanol, most preferably ethanol, and heated, preferably to reflux temperature. After the reaction has taken place the solvent is eliminated in vacuo and the resulting ethyl 3-(2-ethoxycarbonylethyl)amino-2,2-dimethylbutanoate 5 is isolated.

In the subsequent, third reaction step, the ethyl 3-(2-ethoxycarbonylethyl)amino-2,2-dimethylbutanoate derivative 5 resulting from the preceding reaction step—e.g. ethyl 3-(2-ethoxycarbonylethyl)amino-4-(3-methoxyphenyl)-2,2-dimethylbutanoate in the case of the synthesis of BIII 277—is cyclised to form the corresponding piperidone—5-carboethoxy-3,3-dimethyl-2-(3-methoxyphenyl)methyl-4-piperidone—6 in the case of the preparation of BIII 277:

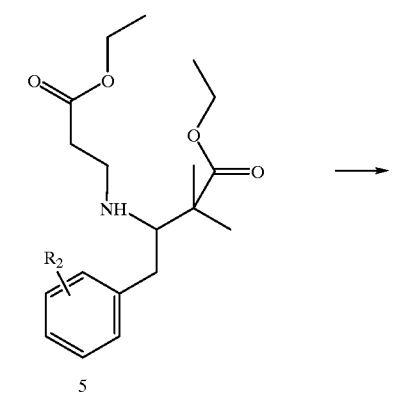

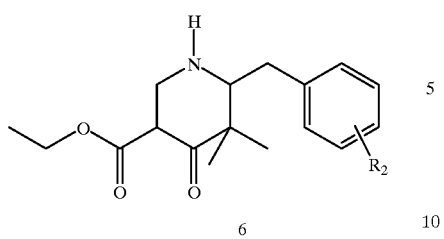

5

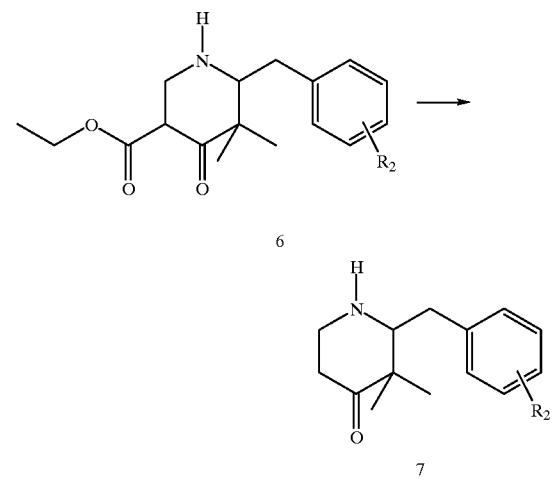

In order to carry out the cyclisation step, which is a type of Dieckmann ester condensation, the ethyl 3-(2-ethoxycarbonylethyl)amino-2,2-dimethylbutanoate derivative 5 is dissolved in a solvent which is inert under the conditions of cyclisation—preferably in an aliphatic or aromatic hydrocarbon, most preferably in toluene—and heated to reflux temperature in the presence of a basically reacting compound, preferably an alkali metal alkoxide of a branched or unbranched $C_{1-4}$-alcohol, most preferably potassium tert.-butoxide, and the components of the reaction mixture which are volatile at these temperatures are eliminated by distillation, e.g. within the scope of an azeotropic reaction. After the reaction has ended, the reaction mixture is hydrolysed and combined with the aqueous solution of an acidically reacting compound, preferably with aqueous inorganic acids, most preferably with concentrated hydrochloric acid. Then an extracting agent which is inert under these conditions and immiscible with water, preferably a dialkylether, most preferably diethylether, is added and combined with the aqueous solution of a basically reacting compound, preferably with aqueous ammonia solution, most preferably with concentrated ammonia solution. After the organic phase has been separated off and the aqueous phase has been extracted exhaustively, the combined organic extracts are washed with water and dried in vacuo and evaporated down and the resulting piperidone of type 6 (namely the 5-carboethoxy-3,3-dimethyl-2-(3-methoxyphenyl)methyl-4-piperidone, in the case of the production of BIII 277—is isolated. Alternatively, the Dieckmann condensation described above may also be carried out using titanium tetrachloride in a halogenated hydrocarbon, preferably dichloromethane [M. N. Deshmukh et al., Synth. Commun. 25 (1995) 177].

In the fourth reaction step, the piperidone derivative 6 is saponified under alkaline or acid conditions and decarboxylated to obtain the corresponding 3,3-dimethyl-4-piperidone derivative 7. The choice of reaction conditions will depend on the chemical nature of the starting material; thus, for example, when preparing BIII 277, the work is done under the conditions of alkaline saponification, resulting in 2-(3-methoxyphenyl)methyl-3,3-dimethyl-4-piperidone, which can be isolated in the form of an acid addition salt, preferably in the form of its hydrohalide:

For this purpose the piperidone ester derivative 6 is heated in a polar, aqueous solvent or mixture of solvents—preferably in a mixture of straight-chained or branched $C_{1-4}$-alkanol and water, most preferably in an ethanol/water mixture—with a basically or acidically reacting compound—preferably with an alkali metal hydroxide or an inorganic acid, most preferably with sodium hydroxide or, if an acid is used, for example, in the presence of hydrochloric acid or sulphuric acid; preferably, the mixture is heated to reflux temperature. After saponification has occurred the reaction medium is eliminated in vacuo and the residue is taken up in a solvent which is suitable for subsequent salt formation, preferably a polar organic solvent, most preferably acetone, and the acid addition salt is precipitated.

The subsequent cleaving of the resulting mixture of the enantiomeric 3,3-dimethyl-4-piperidone—in the case of BIII 277, 2-(3-methoxyphenyl)-methyl-3,3-dimethyl-4-piperidone-hydrochloride—of type 7 is carried out by the known methods of enantiomer separation, e.g. by reacting with malic acid, tartaric acid, mandelic acid or camphor sulphonic acid, tartaric acid being preferred:

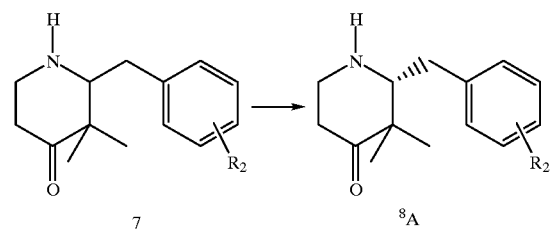

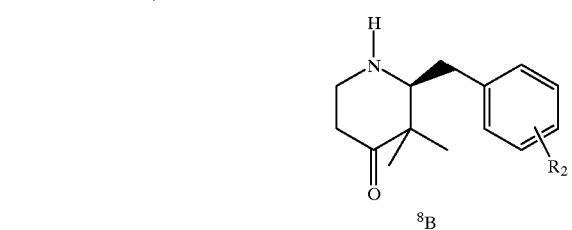

In this way, the reaction with D-(-)-tartaric acid yields the corresponding enantiomerically pure 3,3-dimethyl-4-piperidone derivative of type 8aA or 8B in the form of the hydrogen tartrate thereof, and in the case of BIII 277, for example, (+)-2-(3-methoxyphenyl)-methyl-3,3-dimethyl-4-piperidonium hydrogen tartrate ($R_2$=meta-methoxy).

In order to separate the isomers, for example via the corresponding tartrates, the piperidone derivative 7 in the form of its acid addition salt, e.g. the hydrochloride, is dissolved in water and mixed with a basically reacting compound or, preferably the aqueous solution thereof; it is particularly preferable to use concentrated aqueous ammonia solution. The aqueous phase is extracted with an organic, water-immiscible solvent, preferably with a haloalkane, most preferably dichloromethane. After drying and evaporation in vacuo, the residue is dissolved in a reaction medium which is inert under the reaction conditions used for salt formation, preferably in a branched or unbranched $C_{1-4}$-alkanol, most preferably in ethanol, and mixed with the appropriate stereoisomer of one of the above-mentioned acids, such as D-(-)-tartaric acid. If desired, a sufficient quantity of a nonsolvent—preferably a branched or unbranched $C_{3-8}$-alkanol, most preferably isopropanol—with regard to the desired salt—preferably the corresponding hydrogen tartrate, is added, whereupon the enantiomerically pure isomer of the piperidone crystallises out as the piperidonium hydrogen tartrate; i.e. in the preparation of BIII 277, the corresponding (+)-2-(3-methoxyphenyl) methyl-3,3-dimethyl-4-piperidonium hydrogen tartrate ($R_2$= meta-methoxy).

It has now, surprisingly, been found that after heating the mother liquor which predominantly contains the other enantiomer, a fresh attempt at crystallisation under analogous conditions will again yield a large amount of the desired enantiomer, e.g. in the form of its hydrogen tartrate. Thermal racemisation of the unwanted enantiomer and subsequent recovery of the desired stereoisomer can certainly be carried out several times. In this way, in the case of (+)-2-(3-methoxyphenyl)-methyl-3,3-dimethyl-4-piperidonium hydrogen tartrate, the total yield of desired isomer can be increased to more than 75%.

The subsequent Wittig reaction with methyltriphenylphosphonium bromide leads, in the next step, to the corresponding 4-methylene-piperidine derivative 9—in the case of BIII 277, (+)-2-(3-methoxyphenyl)methyl-3,3-dimethyl-4-methylene-piperidine ($R_2$=meta-methoxy)— which may be isolated in the form of its acid addition salt, preferably in the form of a hydrohalide, most preferably in the form of its hydrochloride.

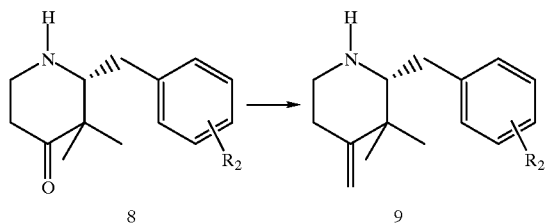

8                                 9

In order to carry out the Wittig reaction the 3,3-dimethylpiperidone derivative 8 is dissolved in water in the form of its acid addition salt, e.g. the hydrochloride, and mixed with a basically reacting compound or, preferably, an aqueous solution thereof; it is particularly preferable to use concentrated aqueous ammonia solution. The aqueous phase is extracted with an organic, water-immiscible solvent, preferably a haloalkane, most preferably dichloromethane. After drying and evaporation in vacuo, the residue is taken up in a reaction medium which is inert under the reaction conditions used for the Wittig reaction, preferably a cyclic ether, most preferably tetrahydrofuran, and mixed with a Wittig reagent which generates a methylene group—preferably a methyltriphenylphosphonium halide, most preferably methyltriphenylphosphonium bromide—in the presence of a basically reacting compound, preferably an alkali metal alkoxide, most preferably potassium tert.-butoxide, and reacted at a temperature in the range from 0 to 80° C.—depending on the reactivity of the educts used— preferably in the range from 20 to 60° C. and most preferably at about 40° C. After the reaction has ended the reaction mixture is mixed with water and a water-immiscible organic solvent, preferably a haloalkane, most preferably dichloromethane, and the organic phase is separated. After the aqueous phase has been extracted exhaustively and the combined extracts have been dried, the extracting agent is eliminated, the residue is dissolved with a solvent suitable for forming an acid addition salt, preferably in a branched or unbranched $C_{1-4}$-alkanol, most preferably isopropanol, and mixed with a suitable acid, preferably an inorganic acid, such as a hydrohalic acid, most preferably concentrated hydrochloric acid, and the acid additiion salt of the Wittig product 9 which crystallises out is isolated.

In the subsequent 7th stage of the reaction the piperidine nitrogen is formylated, e.g. with n-butylformate, resulting in the corresponding enantiomerically pure N-formyl-3,3-dimethyl-4-methylene-piperidine derivative of type 10—in the manufacture of BIII 277, the corresponding (+)-N-formyl-2-(3-methoxyphenyl)methyl-3,3-dimethyl-4-methylene-piperidine ($R_2$=meta-methoxy):

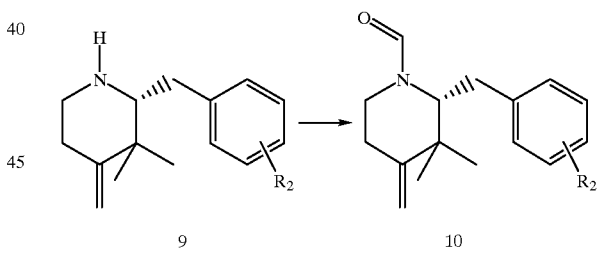

9                                 10

To do this, the piperidine derivative of type 9 which was isolated as the hydrohalide in the proceeding stage, is first converted into the corresponding free base, for example by dissolving the piperidine derivative 9 in the form of its hydrohalide in water and mixing it with a basically reacting compound, preferably with the aqueous solution of a basically reacting compound and most preferably with concentrated ammonia solution, and extracting the free piperidine with an organic solvent, preferably a halogenated hydrocarbon and most preferably with dichloromethane. After the extract has been dried and the extracting agent distilled off, the free base is taken up in an organic solvent such as a hydrocarbon, preferably in an alkyl aromatic compound, most preferably in toluene, and reacted with a formylating agent, preferably an alkylformate, most preferably n-butylformate, and the reaction product is isolated.

In the subsequent reaction of cyclisation, at the 8th stage of the reaction, the benzomorphan structure is finally synthesised, in the presence of correspondingly reactive Lewis acids, most preferably in the presence of aluminium (III)halides, and especially in the presence of aluminium trichloride, and in the case of the preparation of BIII 277 this leads to the corresponding (-)-2-formyl-3'-methoxy-5,9,9-trimethyl-6,7-benzomorphan (11) (R$_2$=meta-methoxy).

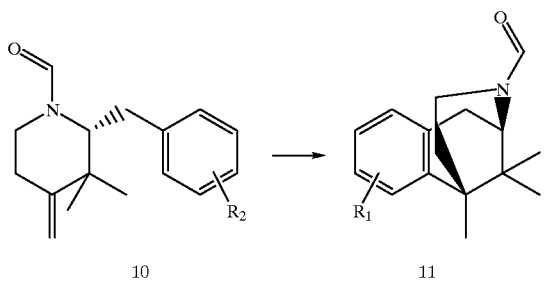

10      11

For this purpose the piperidine derivative 10 is added to a suspension of the above-mentioned Lewis acid, for example in the presence of aluminium(III)chloride, in a solvent which is inert under the reaction conditions chosen, preferably in a halogenated hydrocarbon, most preferably in dichloromethane. After the cyclisation reaction has ended the reaction mixture is carefully hydrolysed. Then the aqueous phase is separated off and extracted. The combined organic phases are dried and evaporated down and the benzomorphan derivative of type 11 is isolated.

It has been found, surprisingly, that when the cyclisation reaction is carried out—by contrast to the established processes of the prior art—using AlCl$_3$, the cyclisation product is obtained in a virtually quantitative yield. When the phenyl system is meta-substituted the process according to the invention also has the advantage that the cyclisation occurs selectively in the para-position, based on the position of R$_2$.

The ninth reaction step which follows results in the cleaving of the formyl group and thus leads to the corresponding 3'-methoxy-5,9,9-trimethyl-6,7-benzomorphan 12.

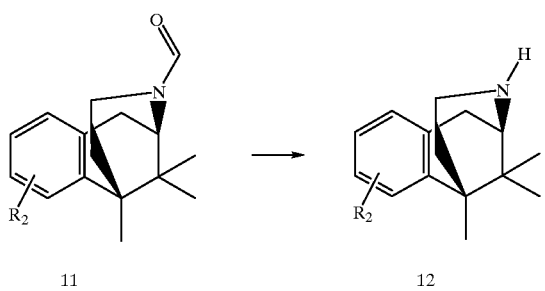

11      12

For this, the formylbenzomorphan 11 is dissolved in a polar solvent, preferably in an alkanol, most preferably in n-propanol, and mixed with an acidically reacting compound, preferably with the aqueous solution of an inorganic acid, most preferably with concentrated hydrochloric acid, and then warmed. After the formyl group has been cleaved the reaction mixture is evaporated down and mixed with water and extracted with a water-immiscible solvent, preferably with an ester of a carboxylic acid, most preferably ethyl acetate. The aqueous phase thus purified is preferably made basic with concentrated ammonia solution and extracted with an organic solvent, preferably with a halohydrocarbon, most preferably with dichloromethane. After the drying and evaporation of the combined organic extracts, the corresponding (-)-3'-methoxy-5,9,9-trimethyl-6,7-benzomorphan (R$_2$=m-CH$_3$O) may be obtained in this way, for example.

At this stage, if desired, chemical modification of the substituent (R$_2$) at the phenyl structure may take place; if not, R$_2$ will have the same meaning as R$_1$. Thus, the benzomorphan derivative 12 resulting from the preceding reaction step may be subjected to ether splitting under acid conditions, preferably with an inorganic acid such as hydrohalic acid and most preferably with hydrobromic acid, resulting in the corresponding free phenol partial structure.

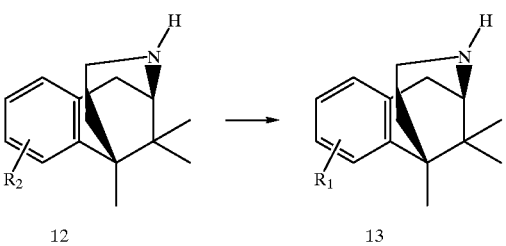

12      13

Ether splitting is carried out under acid conditions, and the use of mineral acids has proved advantageous. It has proved particularly beneficial to use hydrobromic acid, in the case of (-)-3'-methoxy-5,9,9-trimethyl-6,7-benzomorphan. The saponification product resulting from this reaction of saponification can thus be obtained in the form of its hydrobromide [(-)-3'-hydroxy-5,9,9-trimethyl-6,7-benzomorphan-hydrobromide] in a crystalline modification. □

EXAMPLES

1st Reaction step

Ethyl 3-amino-4(3-methoxyphenyl) -2-dimethylbutanoate (4) [R$_2$=m-CH$_3$O]

229.3 g (3.5 mol) of zinc in 3.0 liters of dichloromethane are mixed with 230 ml of trimethylchlorosilane under nitrogen and stirred for 20 minutes at ambient temperature. Then 1.1 liters of absolute tetrahydrofuran are added and the mixture is heated to reflux temperature. To this mixture is added dropwise a mixture of 500 g (2.6 mol) of ethyl bromoisobutyrate (1) and 226.4 g (1.5 mol) of m-methoxybenzylcyanide (2) and the resulting mixture is then refluxed for 1.5 hours. It is allowed to cool, decanted off from the excess zinc and after cooling to about 10° C. mixed with 96.7 g (1.5 mol) of sodium cyanoborohydride. Then 300 ml of ethanol are slowly added dropwise (gas evolved). The reaction is allowed to continue for 20 minutes, 1.0 liters of conc. ammonia solution are added, the phases are separated and the organic phase is washed once more with a mixture of 500 ml of conc. ammonia solution and 500 ml of water. The organic phase is dried over sodium sulphate and evaporated down in vacuo. The residue is taken up in 2.3 liters of toluene and extracted twice with 1.8 liters of 2 N hydrochloric acid. Then the aqueous phase is made alkaline with 700 ml of conc. ammonia solution and extracted twice with 2.2 liters of dichloromethane. After the organic phase has been dried over sodium sulphate it is evaporated down in vacuo. The ethyl 3-amino-4-(3-methoxyphenyl) -2-dimethyl-butanoate (4) is isolated in a yield of 322.5 g (81% of theory) as a yellow oil.

2nd Reaction step

Ethyl 3-(2-ethoxycarbonylethyl)amino-4-(3-methoxyphenyl)-2-dimethylbutanoate (5) [R$_2$=m-CH$_3$O]

382.2 g (1.4 mol) of ethyl 3-amino-4-(3-methoxyphenyl)-2-dimethylbutanoate (4) and 195.4 ml (1.8 mol) of ethyl acrylate are dissolved in 570 ml of absolute ethanol and refluxed for 7 d. The mixture is then evaporated down completely in vacuo. The ethyl 3-(2-ethoxycarbonylethylamino-4-(3-methoxyphenyl)-dimethylbutanoate (5) is isolated in a yield of 469.2 g (89.2% of theory) as a reddish-brown oil.

3rd Reaction step

5-Carboethoxy-3,3-dimethyl-2-(3-methoxyphenyl) methyl-4-piperidone (6) [$R_2$=m-$CH_3O$]

469.2 g (1.3 mol) of ethyl 3-(2-ethoxycarbonylethyl)-amino-4-(3-methoxyphenyl)-2-dimethylbutanoate (5) [$R_2$=m-$CH_3O$] are dissolved in 7.8 liters of toluene and first about 100 ml of a solvent/water mixture are distilled off. The residue is allowed to cool to about 70° C., mixed with 158.3 g (1.4 mol) of potassium tert.-butoxide and heated to 105° C. for 40 minutes, whilst the ethanol formed is distilled off. It is then cooled to 5 C and mixed with 1.2 liters of ice water and 280 ml of conc. hydrochloric acid. 1.2 liters of ether and 220 ml of conc. ammonia solution are added, the organic phase is separated off and the aqueous phase is extracted twice more with 600 ml of diethylether. The combined organic phases are washed twice with 600 ml of water, dried over sodium sulphate and evaporated down in vacuo. The 5-carbethoxy-3,3-dimethyl-2-(3-methoxyphenyl)-methyl-4-piperidone (6) is isolated in a yield of 390.1 g (95.1% of theory) as a reddish-brown oil.

4th Reaction step 2-(3-Methoxyphenyl)methyl-3,3-dimethyl-4-piperidone-hydrochloride (7) [$R_2$=m-$CH_3O$]

390.1 g (1.22 mol) of 5-carboethoxy-3,3-dimethyl-2-(3-methoxyphenyl)methyl-4-piperidone (6) [$R_2$=m-$CH_3O$] are dissolved in a mixture of 204.8 g (5.1 mol) of sodium hydroxide, 680 ml of ethanol and 680 ml of water and refluxed for 20 minutes. The solvent is eliminated in vacuo, the residue is taken up in acetone and the hydrochloride is precipitated with ethereal hydrochloric acid. The 2-(3-methoxyphenyl)methyl-3,3-dimethyl-4-piperidone-hydrochloride (7) is isolated in a yield of 311.9 g (90.1% of theory) in the form of white crystals, m.p. 224–225° C.

5th Reaction step

Enantiomer separation of the piperidone (+)-2-(3-Methoxyphenyl)methyl-3,3-dimethyl-4-piperidonium hydrogen tartrate (8) [$R_2$=m-$CH_3O$]

28.7 g (101 mmol) of 2-(3-methoxyphenyl)methyl-3,3-dimethyl-4-piperidone-hydrochloride (7) are dissolved in 57 ml of water. The aqueous phase is extracted three times with 35 ml of dichloromethane. The combined organic phases are washed with 25 ml of water, then dried with sodium sulphate and the solvent is removed in vacuo. The residue is dried at 80° C. in vacuo until a constant weight is achieved (24.7 g). Then the residue is dissolved warm in 200 ml of ethanol with 15 g (100 mmol) of D-(−)-tartaric acid and 50 ml of isopropanol and a small amount of seed crystals are added with stirring. The mixture is left to crystallise for 24 hours at ambient temperature and suction filtered to remove the crystals (15 g, m.p. 142° C.; $[\alpha]_D^{25}$ =+31.7° (c=1 in MeOH)). The mother liquor is evaporated to dryness in vacuo, combined with 150 ml of a mixture of ethanol and isopropanol (80:20) and refluxed for 20 hours. Then the solution is again mixed with a small amount of seed crystals and left to stand for 6 days. It is then suction filtered again (6.65 g,m.p. 142° C.; $[\alpha]_D^{25}$ =+32.2° (C=1 in methanol)) and the mother liquor is refluxed for a further 20 hours and then evaporated to dryness. The residue is taken up in 100 ml of water, 10 ml of 2 N hydrochloric acid are added and the mixture is extracted three times with 25 ml of diethylether. The ethereal phase is discarded (nonbasic impurities) and the aqueous phase is made alkaline with conc. ammonia solution and extracted three times more with 30 ml of diethylether. The combined ethereal phases are dried over magnesium sulphate and evaporated down in vacuo (10.35 g residue). The residue together with 6.28 g (42 mmol) of D-(+)-tartaric acid is dissolved warm in 104 ml of a mixture of ethanol and isopropanol (80:20). Seed crystals are added and the mixture is left to crystallise for 1 d at ambient temperature. The crystals are suction filtered (5.8 g, m.p. 142° C., $[\alpha]_D^{25}$=+31.6° (C=1 in methanol)). The mother liquor is evaporated down and the residue (11.5 g) is dissolved in 72 ml of a mixture of ethanol and isopropanol (80:20) and refluxed for 20 hours. Then seed crystals are added and the mixture is allowed to stand for 6 days at ambient temperature. The crystals precipitated are suction filtered (2.66 g,m.p. 140° C.; $[\alpha]_D^{25}$ =+31.8° (C=1 in methanol) and combined with the previous fractions. In this way (+)-2-(3-methoxyphenyl)methyl-3,3-dimethyl-4-piperidonium hydrogen tartrate (8) is obtained in a total yield of 30.11 g (75% of theory). □

6th Reaction step (+)-2-(3-Methoxyphenyl)methyl-3,3-dimethyl-4-methylene-piperidine hydrochloride (9)

24.0 g (60.3 mmol) of (+)-2-(3-methoxyphenyl)methyl-3,3-dimethyl-4-piperidonium hydrogen tartrate (8) are dissolved in 50 ml of water and combined with 15 ml of conc. ammonia solution and 50 ml of dichloromethane. The phases are separated, the aqueous phase is extracted twice with 25 ml of dichloromethane and the combined organic phase is dried over magnesium sulphate. Then the solvent is removed in vacuo and the residue is taken up in 30 ml of absolute tetrahydrofuran.

25.7 g (720 mmol) of methyltriphenylphosphonium bromide are suspended in 205 ml of absolute tetrahydrofuran and combined under nitrogen with 8.1 g (720 mmol) of potassium tert.-butoxide at ambient temperature. The mixture is stirred for 30 minutes at 40° C., cooled down to ambient temperature once more and within 10 minutes combined with the above prepared solution of the piperidone in 30 ml of tetrahydrofuran. The resulting mixture is left to react for 1 hour at ambient temperature, cooled to 10° C. and then mixed with 66 ml of water within 15 minutes. The tetrahydrofuran is then eliminated in vacuo and the residue is mixed with 46 ml of dichloromethane and 30 ml of ice water. The phases are separated, the aqueous phase is extracted twice more with 15 ml of dichloromethane and the combined organic extracts are extracted once more with 40 ml of water. Then the mixture is dried over magnesium sulphate, the solvent is eliminated in vacuo, the residue is dissolved in 85 ml of isopropanol and 5.7 ml of conc. hydrochloric acid are added whilst cooling with ice. After 1 hour the mixture is suction filtered (8.5 g), the mother liquor is mixed with 150 ml of diethylether for recrystallisation and after 1 hour it is suction filtered again (5.2 g). The mother liquor is evaporated down in vacuo, the residue is taken up in 30 ml of isopropanol once more and mixed with 200 ml of diethylether. After 3 hours' crystallisation at ambient temperature it is suction filtered (2.1 g) and subsequently all the crystallisation fractions are dried at 60° C. All three fractions proved to be identical according to thin layer chromatography (dichloromethane:methanol:conc. ammonia=95:5:0.1).

In this way the (+)-2-(3-methoxyphenyl)-methyl-3,3-dimethyl-4-methylene-piperidine (9) is isolated in the form of its hydrochloride in a yield of 15.8 g (93.2% of theory), m.p. 199–200°; $[\alpha]_D^{25}$ =+59.9° (C=1 in methanol).

7th Reaction step (+)-N-Formyl-2-(3-methoxyphenyl)methyl-3,3-dimethyl-4-methylene-piperidine (10) [$R_2$=3-CH$_3$O)]

12.7 g (45 mmol) of (+)-2-(3-methoxyphenyl)methyl-3,3-dimethyl-4-methylene-piperidine-hydrochloride (9) are dissolved in 50 ml of water and combined with 8 ml of conc. ammonia. The mixture is extracted three times with 20 ml of dichloromethane, dried over magnesium sulphate and the solvent is eliminated in vacuo. The residue is taken up in 15 ml of toluene and evaporated down once more, taken up again in 75 ml of toluene and refluxed for 4 hours with 23.1 g (22 g mmol) of n-butylformate. The mixture is then evaporated down in vacuo, after which 12.2 g (99.5% of theory) of (+)-N-formyl-2-(3-methoxyphenyl)methyl-3,3-dimethyl-4-methylene piperidine (10) are left in the form of an oil $[\alpha]_D^{25}$ =+52.0° (C=1 in methanol).

8th Reaction step (−)-2-Formyl-3'-methoxy-5,9,9-trimethyl-6,7-benzomorphan (11) [$R_2$=3'-CH$_3$O]

16 g (120 mmol) of aluminium chloride are placed in 140 ml of dichloromethane at a temperature of −10° C. and 10.9 g (40 mmol) of (+)-N-formyl-2-(3-methoxyphenyl)-methyl-3,3-dimethyl-4-methylene piperidine—dissolved in 35 ml of dichloromethane—are added dropwise so slowly that the temperature does not rise above −5° (about 45 min.). Then the mixture is left to react for 30 minutes at 0° C., poured onto 100 g of ice and stirred vigorously. The organic phase is separated off, the aqueous phase is extracted twice more with 30 ml of dichloromethane, the combined organic extracts are dried and the solvent is eliminated in vacuo.

In this way the (−)-2-formyl-3'-methoxy-5,9,9-trimethyl-6,7-benzomorphan (11) is obtained in a yield of 10.9 g (99.6% of theory in the form of an oil; $[\alpha]_D^{25}$=−198.4° (C=1 in methanol)).

9th Reaction stop (−)-3'-Methoxy-5,9,9-trimethyl-6,7-benzomorphan (12) [$R_2$=3'-CH$_3$O]

9.57 g (35 mmol) of (−)-2-formyl-3'-methoxy-5,9,9-trimethyl-6,7-benzomorphan (11) are dissolved in 75 ml of n-propanol and refluxed with 25 ml of conc. hydrochloric acid and 14.3 ml of water for 14 hours. The mixture is then evaporated down in vacuo, the residue is taken up in 50 ml of ice water and extracted three times with 20 ml of ethyl acetate (discarded). The aqueous phase is combined with 55 ml of conc. ammonia and extracted three times with 25 ml of dichloromethane. The combined organic extracts are dried over magnesium sulphate and evaporated down in vacuo. In this way the (−)-3'-methoxy-5,9,9-trimethyl-6,7-benzomorphan (11) is isolated in a yield of 7.9 g (92.0% of theory) as an oil; $[\alpha]_D^{25}$=−66.0° (C=1 in methanol).

10th Reaction step (−)-3'-Hydroxy-5,9,9-trimethyl-6,7-benzomorphan-hydrobromide (13) [$R_1$=3'-OH]

10 g (41 mmol) of (−)-3'-methoxy-5,9,9-trimethyl-6,7-benzomorphan (12) are refluxed for 2 hours with 22.5 ml of water and 77.5 ml of 62% hydrobromic acid. Then the mixture is evaporated down in vacuo and the residue is recrystallised from about 80 ml of acetone, after which 11.8 g (92.8% of theory) of (−)-3'-hydroxy-5,9,9-trimethyl-6,7-benzomorphan-hydrobromide (13) are obtained in the form of crystals, m.p.>290° C.; $[\alpha]_D^{25}$=−55.8° (C=1 in methanol).

We claim:

1. Process for preparing norbenzomorphans of general formula 1

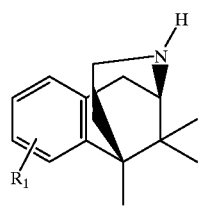

wherein $R_1$ denotes hydrogen, $C_{1-6}$-alkyl, halogen, hydroxy, $C_{1-8}$-alkoxy, a benzoyl group bound via an oxygen or an alkylcarboxyl group having a straight-chained or branched $C_{1-6}$-lower alkyl group—wherein the alkyl group may optionally be substituted by one or more halogen atoms which may be identical or different nitro, cyano, $NH_2$, $NH(C_{1-8}$-alkyl), $N(C_{1-8}$-alkyl)$_2$, wherein the alkyl groups may be identical or different, NH-acyl-($C_{1-8}$-alkyl), wherein acyl denotes benzoyl or an alkylcarbonyl group having a straight-chained or branched $C_{1-6}$-lower alkyl group, whilst the alkyl group may optionally be substituted by one or more halogen atoms which may be the same as one another or different from one another, characterised in that a) a benzylcyanide of general formula 2 is subjected to the conditions of a Reformatsky reaction with ethyl bromoisobutylbutyrate (3) in the presence of an alkylhalosilane and zinc powder in an inert solvent in the presence of a reducing agent which is selective with regard to the reduction of imino functions, and the resulting ethyl 3-amino-2,2-dimethylbutanoate derivative of general formula 4 is isolated

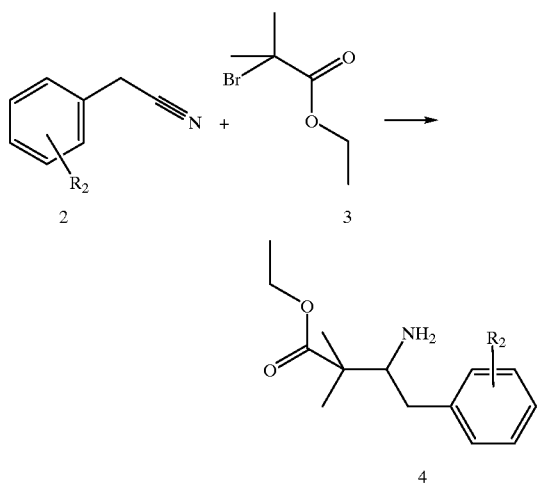

and b) the ethyl 3-amino-2,2-dimethylbutanoate derivative of general formula 4 is subjected to the conditions of a Michael addition reaction with ethyl acrylate and the resulting ethyl 3-(2-ethoxycarbonylethyl)amino-2,2-dimethylbutanoate derivative of general formula 5 is isolated general formula 7, isolated and if desired the corresponding acid addition salt is prepared using an acid and isolated

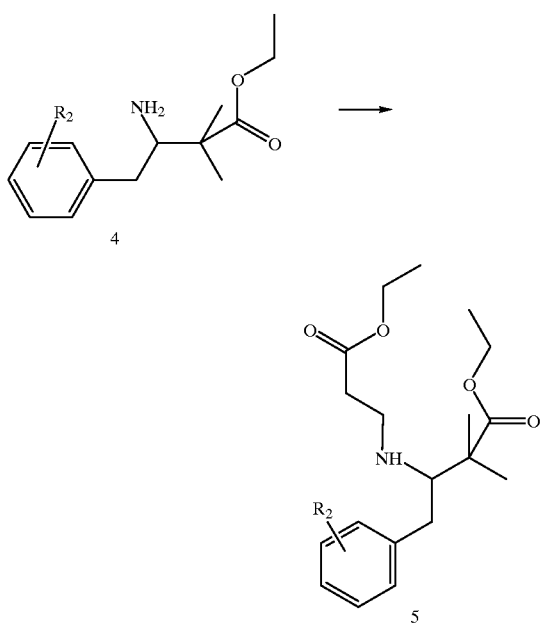

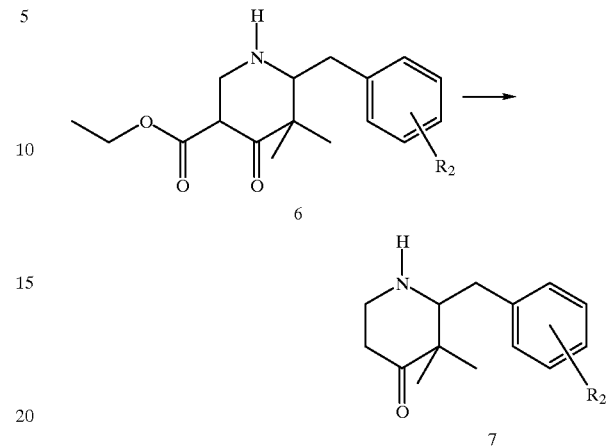

and e) the stereoisomer mixture thus obtained is dissolved, optionally after release of the enantiomeric free bases, in a reaction medium which is inert with respect to enantiomer separation, then combined with a suitable stereoisomer of an organic acid suitable for salt formation with a stereoisomer of the mixture of enantiomers, the desired stereoisomer is isolated in the form of its addition salt with the optically active acid, the mother liquor containing the unwanted isomer is heated and in this way the unwanted enantiomer is converted thermally into the desired stereoisomer, mixed with an optically active enantiomerically pure organic acid capable of forming an acid addition salt and the desired stereoisomer thus present as an acid addition salt is optionally added, with the addition of a medium which behaves as a nonsolvent relative to the desired salt, and then isolated and this process is repeated as necessary c) the ethyl 3-(2-ethoxycarbonylethyl)amino-2,2-dimethylbutanoate of general formula 5 thus prepared is subjected to the conditions of a Dieckmann ester condensation in an inert solvent in the presence of a basically reacting compound and the resulting piperidone derivative of general formula 6 is isolated

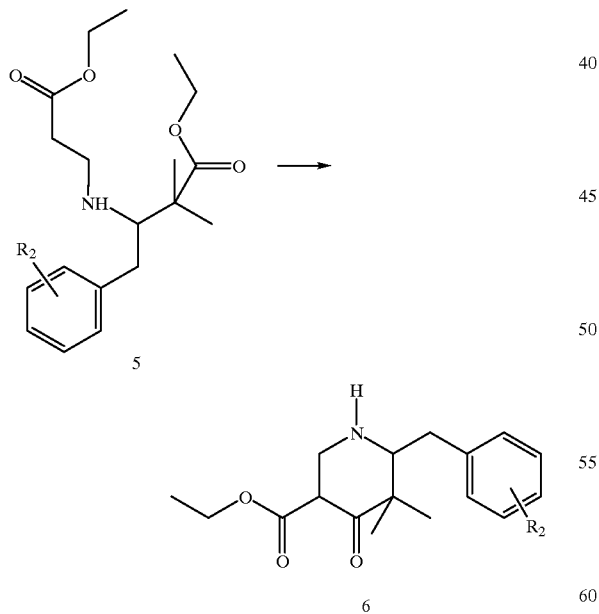

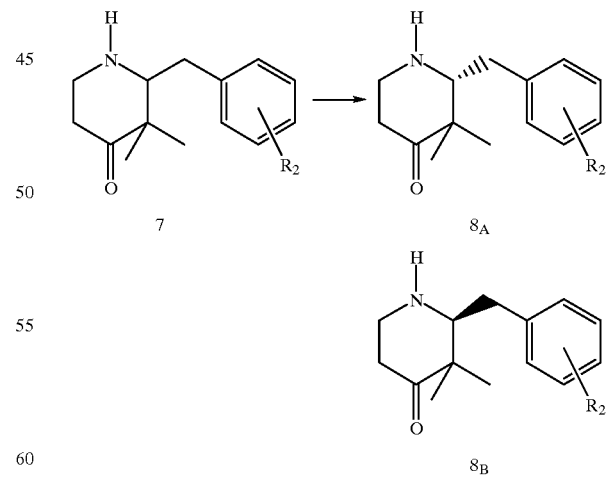

and d) the piperidone derivative 6 is saponified under acid or alkaline conditions in a polar solvent or solvent mixture, with heating, then decarboxylated, to obtain the corresponding 3,3-dimethylpiperidone derivative of and f) the pure stereoisomer thus obtained, after release from the enantiomerically pure acid addition salt, is reacted in an inert solvent with a Wittig reagent generating a methylene group in the presence of a basically reacting compound and the reaction product of type 9 or the corresponding stereoisomer is isolated, optionally in the form of the acid addition salt thereof

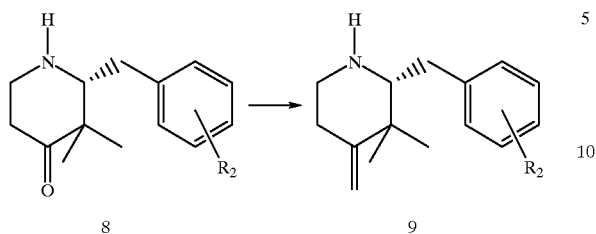

and g) the alkene 9 obtained from the Wittig reaction is optionally first freed from its acid addition salt and the free base of type 9 is dissolved in an organic solvent and subjected, with a formylating agent, to a formylating reaction at the piperidine nitrogen and the reaction product of type 10 or the corresponding stereoisomer thereof is isolated

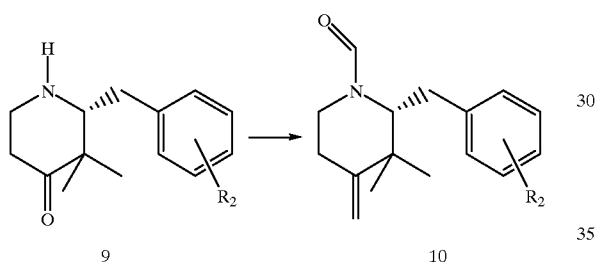

and h) the formyl compound 10 thus obtained, or the corresponding stereoisomer, is dissolved in an inert solvent and reacted with a Lewis acid and the cyclising product of type 11 resulting from this reaction is isolated

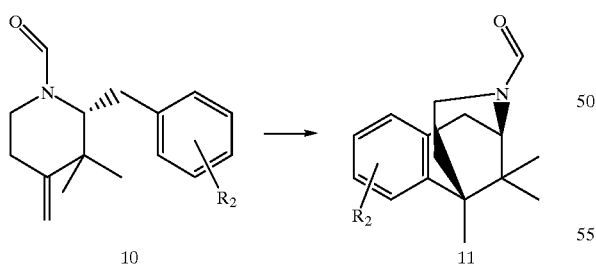

i) the benzomorphan derivative resulting from the cyclising reaction is dissolved in a polar solvent and reacted with an acidically reacting compound and the deformylated norbenzomorphan of type 12 resulting from this reaction is optionally isolated in the form of its acid addition salt

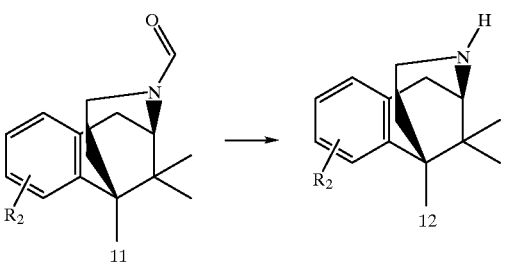

and j) if desired, after liberation of the free benzomorphan base, the substituent $R_2$, if it constitutes an alkoxy group, is converted by ether splitting into a free hydroxy function and the reaction product is isolated, optionally in the form of the acid addition salt thereof of type 13, the base corresponding to general formula 1.

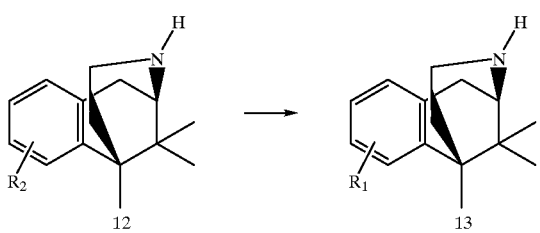

2. Process for preparing norbenzomorphan of general formula 1 according to claim 1

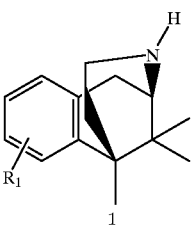

wherein $R_1$ denotes hydrogen, $C_{1-6}$-alkyl, halogen, hydroxy, $C_{1-8}$-alkoxy, a benzoyl group bound via an oxygen or an alkylcarboxyl group having a straight-chained or branched $C_{1-6}$-lower alkyl group—wherein the alkyl group may optionally be substituted by one or more halogen atoms which may be identical or different nitro, cyano, $NH_2$, $NH(C_{1-8}$-alkyl), $N(C_{1-8}$-alkyl)$_2$, wherein the alkyl groups may be identical or different, NH-acyl-($C_{1-8}$-alkyl), wherein acyl denotes benzoyl or an alkylcarbonyl group having a straight-chained or branched $C_{1-6}$-lower alkyl group, whilst the alkyl group may optionally be substituted by one or more halogen atoms which may be the same as one another or different from one another, characterised in that a) a benzylcyanide of general formula 2 is reacted with ethyl bromoisobutylbutyrate (3) in the presence of an alkyl halosilane and zinc powder in an inert solvent, the reaction mixture is heated, allowed to cool after the reaction has ended, the zinc powder is separated off and the reaction mixture is mixed with a reducing agent which is selective with regard to the reduction of imino functions and the reaction mixture is diluted with an alkanol and then mixed with an aqueous solution of a basically reacting compound, the organic phase is removed and evaporated down, the residue is taken up in an inert solvent, the resulting solution is extracted with the aqueous solution of an acid, the combined aqueous extracts are made alkaline with a basically reacting compound, this alkaline solution is extracted with a water-immiscible organic solvent and the resulting ethyl 3-amino-2,2-dimethylbutanoate derivative of general formula 4 is isolated

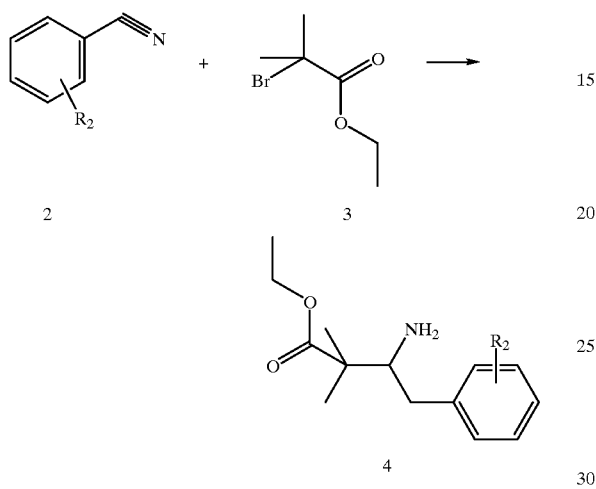

and b) the ethyl 3-amino-2,2-dimethylbutanoate derivative of general formula 4 is subjected with ethyl acrylate to a Michael addition reaction in an inert solvent, the reaction medium is eliminated once the reaction has ended and the resulting ethyl 3-(2-ethoxycarbonylethyl) amino-2,2-dimethylbutanoate derivative of general formula 5 is isolated

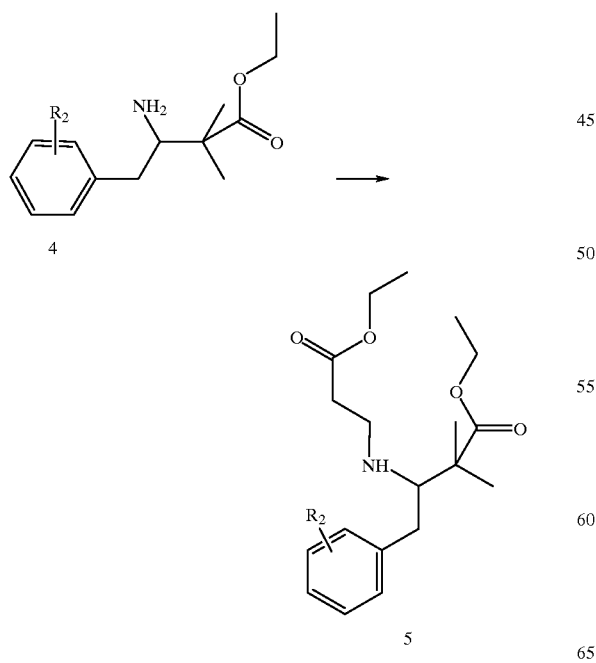

and c) the ethyl 3-(2-ethoxycarbonylethyl) amino-2,2-dimethylbutanoate of general formula 5 thus prepared is subjected to the conditions of a Dieckmann ester condensation in an inert solvent in the presence of a basically reacting compound, the volatile components of the reaction mixture resulting from the reaction of cyclisation are eliminated by distillation, then the mixture is hydrolysed and mixed with the aqueous solution of an acidically reacting compound, the resulting mixture is combined with a water-immiscible organic solvent and an aqueous solution of a basically reacting compound, the combined organic extracts are evaporated down and the resulting piperidone derivative of general formula 6 is isolated

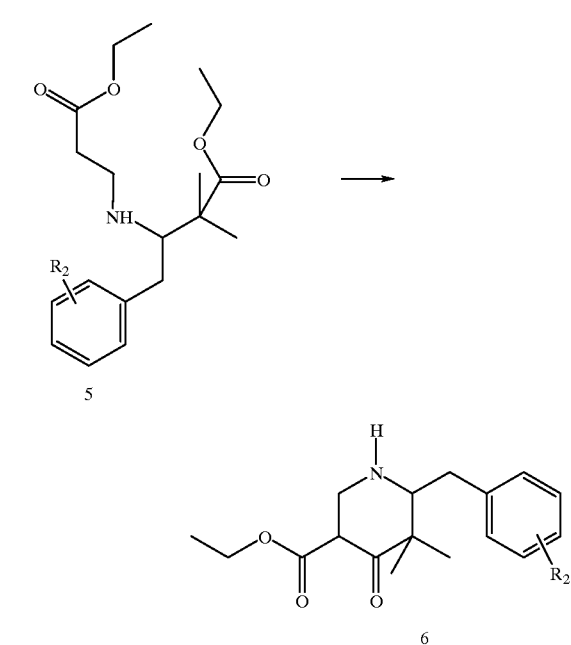

and d) the piperidone derivative 6 is saponified under acid or alkaline conditions in a polar solvent or mixture of solvents, with heating, then decarboxylated, to obtain the corresponding 3,3-dimethylpiperidone derivative of general formula 7 and isolated and if desired the corresponding acid addition salt is prepared using an acid and then isolated □

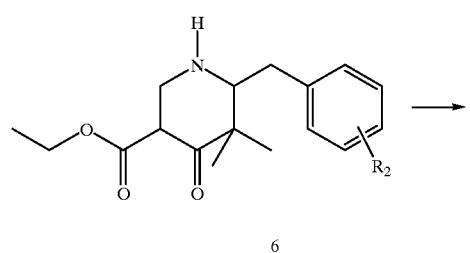

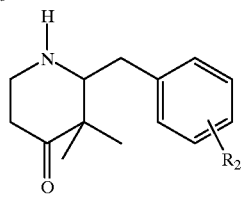

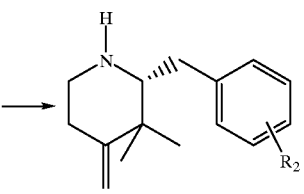

and e) the mixture of stereoisomers thus obtained is dissolved, optionally after liberation of the enantiomeric free bases, in a reaction medium which is inert relative to the enantiomer separation, mixed with a suitable stereoisomer of an organic acid which is suitable for salt formation with a stereoisomer of the enantiomer mixture, the desired stereoisomer is isolated in the form of the acid addition salt thereof with the optically active acid, the mother liquor containing the unwanted isomer is heated and the unwanted enantiomer is thereby converted thermally into the desired stereoisomer, mixed with an optically active, enantiomerically pure, organic acid capable of forming an acid addition salt and the desired stereoisomer, thus present as an acid addition salt, is optionally added, with the addition of a medium which behaves as a nonsolvent relative to the desired salt, and the salt is isolated and this process is repeated as necessary

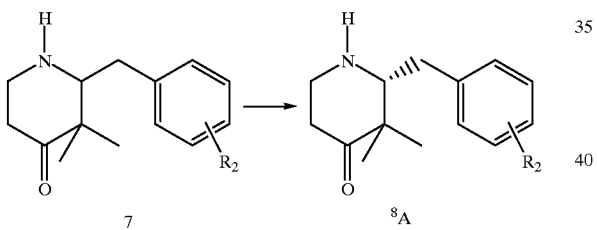

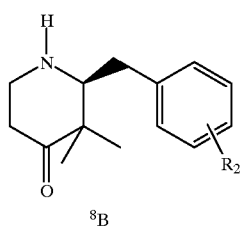

and f) the pure stereoisomer thus obtained, after liberation from the enantiomerically pure acid addition salt, is subjected to a Wittig reaction in an inert solvent with a Wittig reagent generating a methylene group in the presence of a basically reacting compound and in a temperature range from 0 to 80° C., after the reaction the mixture is combined with water and a water-immiscible organic solvent, the aqueous phase is extracted exhaustively, the reaction product of type 9 is isolated or, after the addition of a proton acid, the corresponding stereoisomer is isolated in the form of the acid addition salt thereof □ and g) the alkene 9 obtained from the Wittig reaction is optionally first freed from its acid addition salt and the free base of type 9 is dissolved in an organic solvent and subjected, with a formylating agent, to a formylating reaction at the piperidine nitrogen and the reaction product of type 10 or the corresponding stereoisomer thereof is isolated

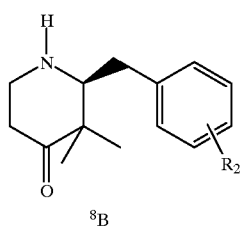

and h) the formyl compound 10 thus obtained, or the corresponding stereoisomer, is dissolved in an inert solvent and reacted with a Lewis acid and the cyclising product of type 11 resulting from this reaction is isolated □

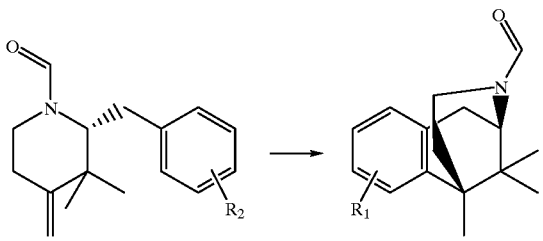

and i) the benzomorphan derivative resulting from the cyclising reaction is dissolved in a polar solvent and reacted with an acidically reacting compound and the deformylated norbenzomorphan of type 12 resulting from this reaction is optionally isolated in the form of its acid addition salt, after the addition of the inorganic acid

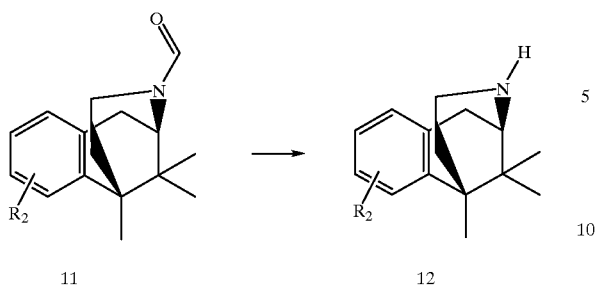

and j) if desired, after liberation of the free benzomorphan base, the substituent $R_2$, if it constitutes an alkoxy group, is converted by ether splitting into a free hydroxy function and the reaction product is isolated, optionally in the form of the acid addition salt thereof of type 13, the base corresponding to general formula 1.

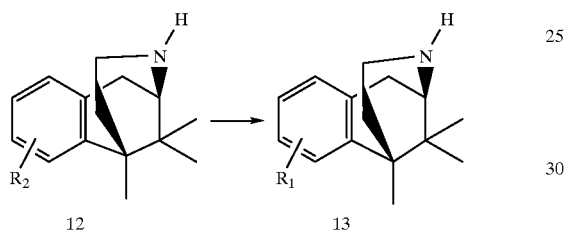

3. Process for preparing norbenzomorphan of general formula 1 wherein $R_1$ is defined as in claim 1, according to claim 2, characterised in that a) a benzylcyanide of general formula 2 is reacted with ethyl bromoisobutylbutyrate (3) in the presence of a trialkylhalosilane and zinc power in an ether and a haloalkane, the reaction mixture is heated, allowed to cool once the reaction has ended, the zinc powder is removed and the reaction mixture is combined with a complex alkali metal borohydride derivative which is selective with regard to the reduction of imino functions, and the reaction mixture is diluted with a $C_{1-4}$-alcohol and then with an aqueous ammonia solution, the organic phase is separated and evaporated down, the residue is taken up in an aliphatic or aromatic hydrocarbon, the solution obtained is extracted with the aqueous solution of an inorganic acid, the combined aqueous extracts are made alkaline with aqueous ammonia solution, this alkaline solution is extracted with a halohydrocarbon and the resulting ether 3-amino-2,2-dimethylbutanoate derivative of general formula 4 is isolated

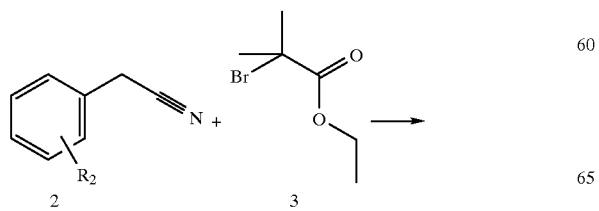

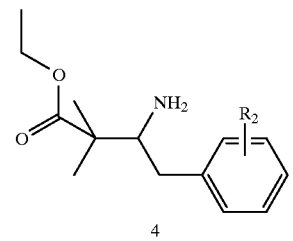

and b) the ethyl 3-amino-2,2-dimethylbutanoate derivative of general formula 4 is subjected to a Michael addition reaction with ethyl acrylate in a straight-chained or branched $C_{1-4}$-alcohol, after the reaction has ended the reaction medium is eliminated and the resulting ethyl 3-(2-ethoxycarbonylethyl)-amino-2,2-dimethylbutanoate derivative of general formula 5 is isolated

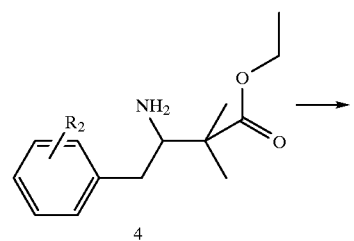

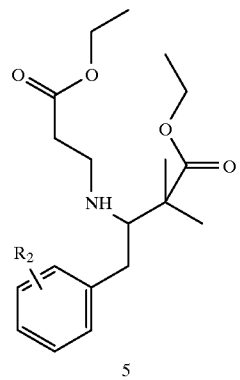

and c) the ethyl 3-(2-ethoxycarbonylethyl)amino-2,2-dimethylbutanoate derivative of general formula 5 thus prepared is subjected to the conditions of a Dieckmann ester condensation in an aliphatic or aromatic hydrocarbon in the presence of an alkali metal alkoxide of a straight-chained or branched $C_{1-4}$-alcohol, the volatile components of the reaction mixture resulting from the reaction of cyclisation are eliminated by distillation, then the mixture is hydrolysed and mixed with the aqueous solution of an inorganic acid, the resulting mixture is combined with a water-immiscible dialkylether and with aqueous ammonia solution, the combined organic extracts are evaporated down and the resulting piperidone derivative of general formula 6 is isolated

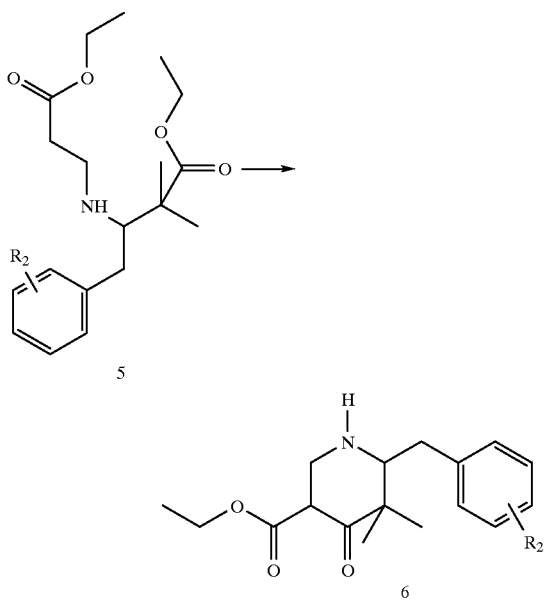

5 and d) the piperidone derivative 6 is saponified in a mixture of a straight-chained or branched $C_{1-4}$-alcohol and water in the presence of an alkali metal hydroxide or an inorganic acid, with heating, and decarboxylated to obtain the corresponding 3,3-dimethylpiperidone derivative of general formula 7, the product is isolated and optionally the corresponding acid addition salt is prepared with a proton acid

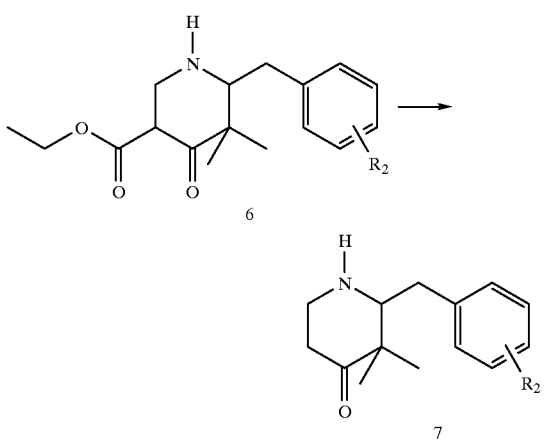

and e) the mixture of stereoisomers thus obtained is dissolved, optionally after liberation of the enantiomeric free bases, in a straight-chained or branched $C_{1-4}$-alcohol, mixed with the corresponding enantiomers of malic, tartaric, mandelic or camphor sulphonic acid, the desired stereoisomer is isolated in the form of its salt of addition with the optically active acid, the mother liquor containing the unwanted isomer is heated and in this way the unwanted enantiomer is thermally converted into the desired stereoisomer, mixed with an optically active, enantiomerically pure organic acid capable of forming an acid addition salt and the desired stereoisomer occurring as an acid addition salt is optionally crystallised by the addition of a $C_{3-8}$-alcohol and then isolated and this procedure is repeated as necessary

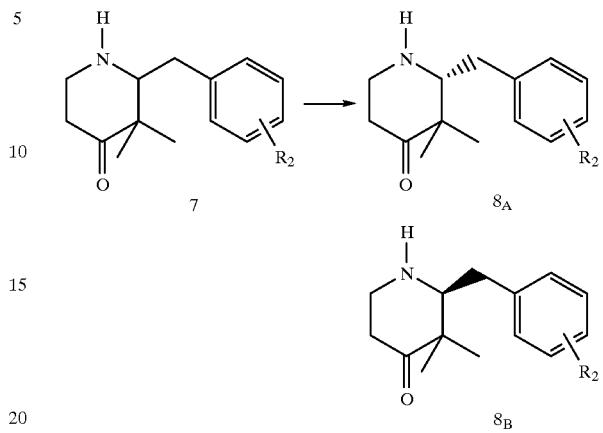

and f) the pure stereoisomer thus obtained is liberated from the enantiomerically pure acid addition salt and then subjected to a Wittig reaction, in an optionally cyclic ether with a methyl triphenylphosphonium halide in the presence of an alkali metal alkoxide in a temperature range from 20 to 60° C., then after the reaction has taken place the reaction mixture is mixed with water and with a haloalkane, the aqueous phase is extracted exhaustively, the reaction product of type 9 or optionally the corresponding stereoisomer is isolated in the form of its acid addition salt after the addition of a proton acid

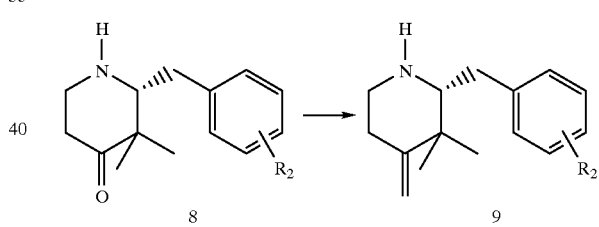

and g) the alkene 9 obtained from the Wittig reaction is optionally first liberated from its acid addition salt and the free base of type 9 is dissolved in an alkyl aromatic compound as solvent and subjected, with an alkyl formate, to a formylation reaction at the piperidine nitrogen and the reaction product of type 10 or the corresponding stereoisomer thereof is isolated

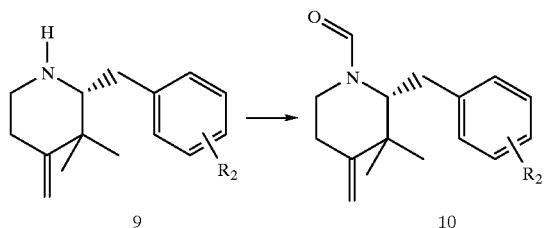

and h) the formyl compound 10 thus obtained, or the corresponding stereoisomer, is dissolved in a halogenated hydrocarbon and reacted with an aluminium(III)halide and the cyclisation product of type 11 resulting from this reaction is isolated

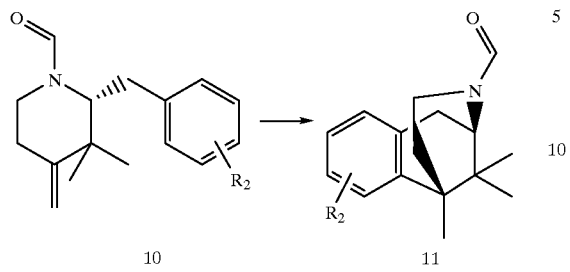

and i) the benzomorphan derivative 11 resulting from the reaction of cyclisation is dissolved in an alkanol and reacted with the aqueous solution of a hydrohalic acid and the deformylated norbenzomorphan of type 12 resulting from this reaction is isolated optionally after the addition of a proton acid, in the form of the acid addition salt thereof

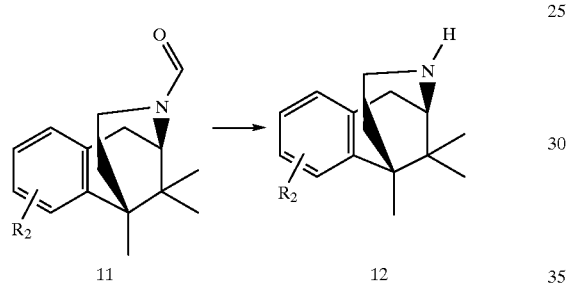

and j) if desired, after liberation of the free benzomorphan base, the substituent $R_2$, if it denotes an alkoxy group, is converted into a free hydroxy function by the method of ether splitting and the reaction product is isolated, optionally in the form of the acid addition salt thereof of type 13, in which the base corresponds to general formula 1

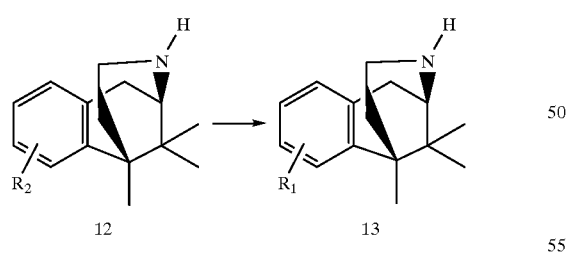

4. Process for preparing norbenzomorphan of general formula 1 wherein $R_1$ is defined as in claim 1, according to claim 3, characterised in that a) a benzylcyanide of general formula 2 is reacted with ethyl bromoisobutylbutyrate (3) in the presence of chlorotrimethylsilane and zinc powder in dichloromethane after diluting with tetrahydrofuran, the reaction mixture is heated, then when the reaction has ended it is allowed to cool, the zinc powder is separated off and the reaction mixture is combined with sodium cyanoborohydride and the resulting mixture is diluted with ethanol and then mixed with concentrated aqueous ammonia solution, the organic phase is separated off and evaporated down, the residue is taken up in toluene, the solution obtained is extracted with 2 N hydrochloric acid, the combined aqueous extracts are made alkaline with concentrated aqueous ammonia solution, this alkaline solution is extracted with dichloromethane and the resulting ethyl 3-amino-2,2-dimethylbutanoate derivative of general formula 4 is isolated

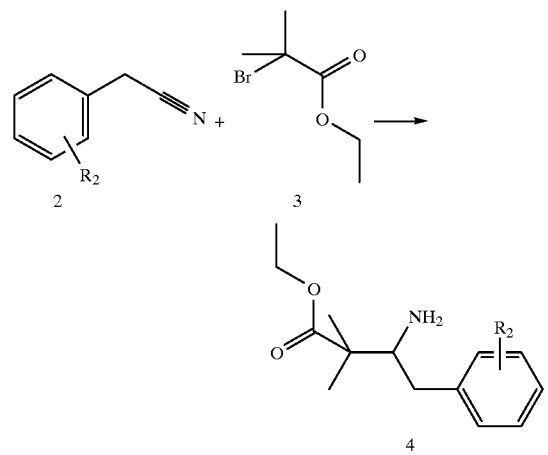

and b) the ethyl 3-amino-2,2-dimethylbutanoate derivative of general formula 4 is subjected to a Michael addition reaction with ethyl acrylate in ethanol as solvent, the reaction medium is removed once the reaction has ended and the resulting ethyl 3-(2-ethoxycarbonylethyl)amino-2,2-dimethylbutanoate derivative of general formula 5 is isolated

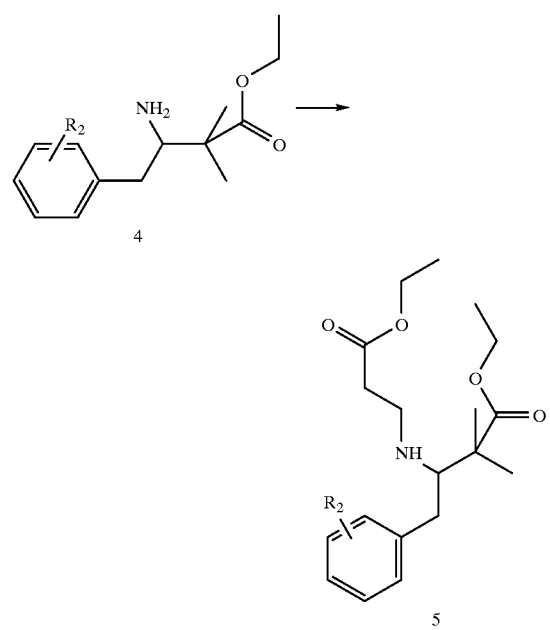

and c) the ethyl 3-(2-ethoxycarbonylethyl)amino-2,2-dimethylbutanoate derivative of general formula 5 thus obtained is subjected to the conditions of a Dieckmann ester condensation in toluene in the presence of potassium tert.-butoxide, the volatile components of the reaction mixture resulting from the reaction of cyclisation are eliminated by distillation, then the mixture is hydrolysed and combined with concentrated hydrochloric acid, the resulting mixture is combined with diethylether and concentrated ammonia solution, the combined organic extracts are evaporated down and the resulting piperidone derivative of general formula 6 is isolated

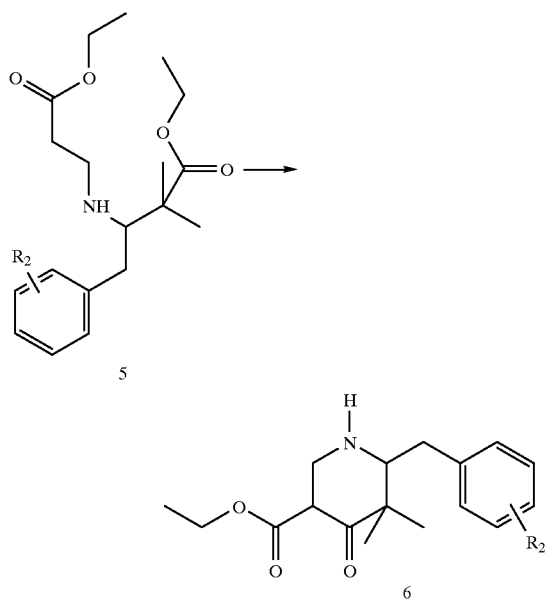

and d) the piperidone derivative 6 is saponified in an ethanol/water mixture in the presence of sodium hydroxide or hydrochloric acid or sulphuric acid, whilst heating to reflux temperature, and decarboxylated to obtain the corresponding 3,3-dimethylpiperidone derivative of general formula 7, the reaction product is isolated and the corresponding hydrohalide is optionally prepared with hydrochloric or hydrobromic acid and e) the mixture of stereoisomers thus obtained is dissolved in ethanol, optionally after liberation of the enantiomeric free bases, mixed with the corresponding enantiomer (D- or L-form) of tartaric acid, the desired stereoisomer is isolated in the form of the corresponding tartrate, the mother liquor containing the unwanted isomer is heated and in this way the unwanted enantiomer is converted thermally into the desired stereoisomer, then mixed with D- or L-tartaric acid and the desired stereoisomer thus present as the corresponding tartrate is optionally crystallised by the addition of isopropanol and the precipitate is isolated and this procedure is repeated as necessary and f) the pure stereoisomer thus obtained, after liberation from the enantiomerically pure acid addition salt, is subjected to a Wittig reaction in tetrahydrofuran with methyl triphenylphosphonium bromide in the presence of potassium tert.-butoxide at a temperature of 40° C., then when the reaction has ended the mixture is combined with water and dichloromethane, the aqueous phase is extracted exhaustively, the reaction product of type 9 or the corresponding stereoisomer is isolated in the form of its hydrohalide and g) the alkene 9 obtained from the Wittig reaction is optionally first liberated from its acid addition salt and the free base of type 9 is dissolved in toluene and subjected with n-butylformate to a reaction of formylation at the piperidine nitrogen and the reaction product of type 10 or the corresponding stereoisomer thereof is isolated

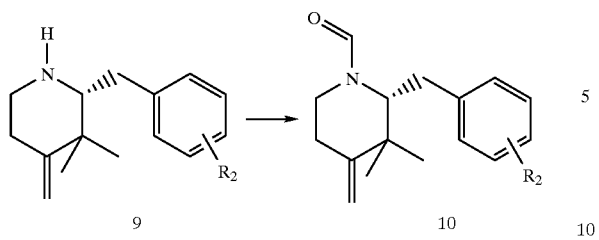

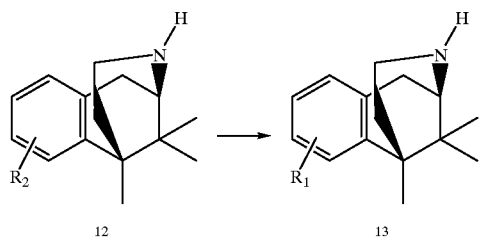

h) the formyl compound 10—or the corresponding stereoisomer—thus obtained is dissolved in dichloromethane and reacted with aluminium(III)chloride at a temperature of not more than −5° C. and the cyclisation product of type 11 resulting from this reaction is isolated

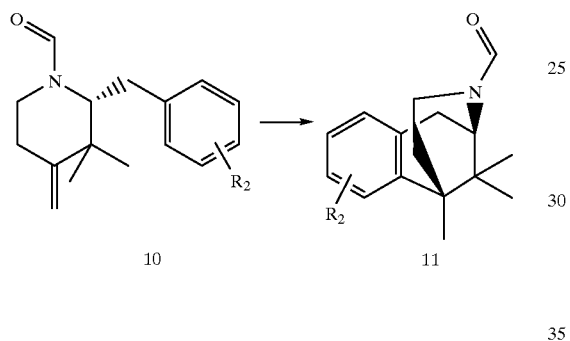

and i) the benzomorphan derivative 11 resulting from the reaction of cyclisation is dissolved in n-propanol and reacted with concentrated hydrochloric acid and the deformylated norbenzomorphan of type 12 resulting from this reaction is isolated in the form of its hydrochloride

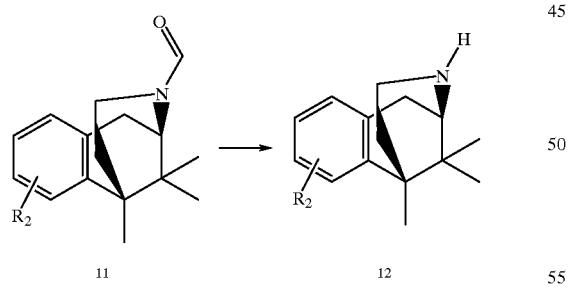

and j) if desired, after liberation of the free benzomorphan base, the substituent $R_2$, if it denotes an alkoxy group, is converted by ether splitting into a free hydroxy function and the reaction product is isolated, optionally after the addition of hydrochloric or hydrobromic acid, in the form of its hydrohalide of general formula 13, the base corresponding to general formula 1.

5. Process for preparing norbenzomorphan of general formula 1 wherein $R_1$ denotes a hydroxy group in the 3'-position, according to claim 4, characterised in that a) a benzylcyanide of general formula 2 wherein $R_2$ denotes a methoxy group in the 3-position is reacted with ethyl bromoisobutylbutyrate (3) in the presence of chlorotrimethylsilane and zinc powder in dichloromethane after dilution with tetrahydrofuran, the reaction mixture is heated, left to cool after the reaction has ended, the zinc powder is separated off and the reaction mixture is combined with sodium cyanoborohydride and then diluted with ethanol and then mixed with concentrated aqueous ammonia solution, the organic phase is separated off and evaporated down, the residue is taken up in toluene, the solution obtained is extracted with 2 N hydrochloric acid, the combined aqueous extracts are made alkaline with concentrated aqueous ammonia solution, this alkaline solution is extracted with dichloromethane and the resulting ethyl 3-amino-4-(3-methoxyphenyl)-2,2-dimethylbutanoate (4, $R_2$=3-OCH$_3$) is isolated

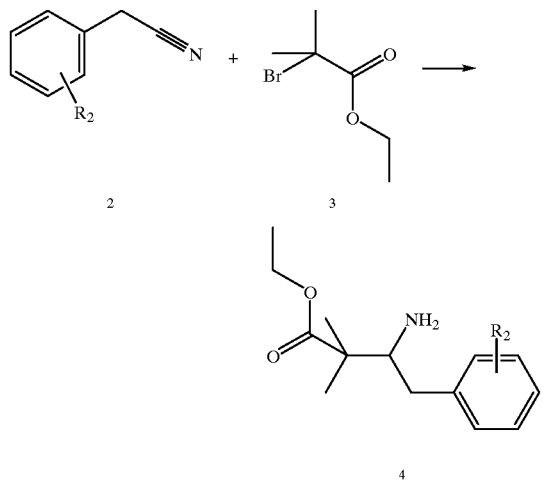

and b) the ethyl 3-amino-4-(3-methoxyphenyl)-2,2-dimethylbutanoate (4, $R_2$=3-OCH$_3$) is subjected with ethyl acrylate to a Michael addition reaction in ethanol as solvent, then when the reaction has ended the reaction medium is eliminated and the ethyl 3-(2-ethoxycarbonylethyl)amino-4-(3-methoxyphenyl)-2,2-dimethylbutanoate (5, $R_2$=3-OCH$_3$) is isolated

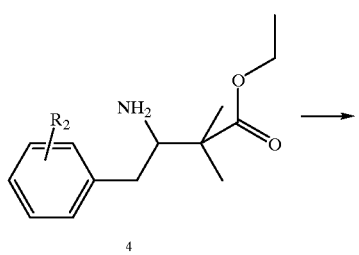

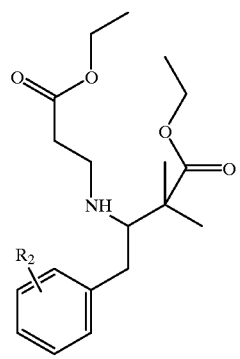

and c) the ethyl 3-(2-ethoxycarbonylethyl)amino-4-(3-methoxyphenyl)-2-dimethylbutanoate (5, R$_2$=3-OCH$_3$) is subjected to the conditions of a Dieckmann ester condensation in toluene in the presence of potassium tert.-butoxide, the volatile components of the reaction mixture resulting from the reaction of cyclisation are removed by distillation, after which the mixture is hydrolysed and mixed with concentrated hydrochloric acid, the resulting mixture is combined with diethyl-ether and with concentrated ammonia solution, the combined organic extracts are evaporated down and the 5-carboethoxy-3,3-dimethyl-2-(3-methoxyphenyl)methyl-4-piperidone (6, R$_2$=3-OCH$_3$) is isolated

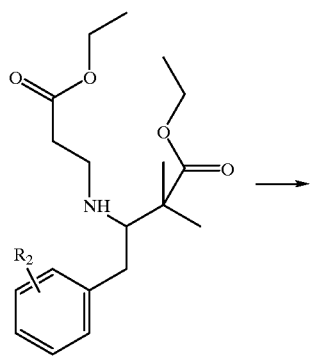

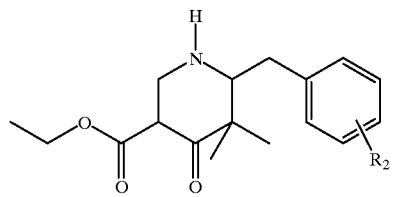

and d) the 5-carboethoxy-3,3-dimethyl-2-(3-methoxyphenyl)methyl-4-piperidone (6, R$_2$=3-OCH$_3$) is saponified in an ethanol/water mixture in the presence of sodium hydroxide or hydrochloric acid or sulphuric acid, with heating to reflux temperature, and decarboxylated to obtain the 2-(3-methoxyphenyl)methyl-3,3-dimethyl-4-piperidone-hydrochloride (7, R$_2$=m-CH$_3$O), the reaction product is isolated and the corresponding 2-(3-methoxyphenyl)methyl-3,3-dimethyl-4-piperidone-hydrochloride is precipitated with hydrochloric acid

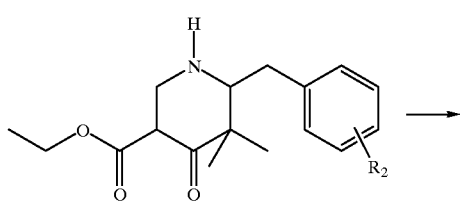

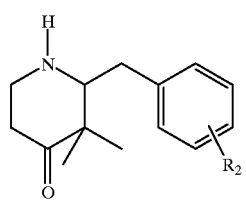

and e) the stereoisomer mixture of the 2-(3-methoxyphenyl)methyl-3,3-dimethyl-4-piperidone-hydrochloride of type 7 (R$_2$=3-OCH$_3$) thus obtained is dissolved in ethanol, after the enantiomeric free bases have been liberated, then mixed with D-(−)-tartaric acid, the desired (+)-2-(3-methoxyphenyl)-methyl-3,3-dimethyl-4-piperidonium hydrogen tartrate of type 8A (R$_2$=3-OCH$_3$) is isolated, the mother liquor containing the unwanted isomer is heated and in this way the unwanted (−)-2-(3-methoxyphenyl)methyl-3,3-dimethyl-4-piperidone (8B, R$_2$=3-OCH$_3$) is thermally converted into the desired (+)-2-(3-methoxyphenyl)methyl-3,3-dimethyl-4-piperidone (8A), mixed with D-(−)-tartaric acid and the desired (+)-2-(3-methoxyphenyl)methyl-3,3-dimethyl-4-piperidonium hydrogen tartrate of type 8A (R$_2$=3-OCH$_3$) is crystallised by the addition of isopropanol and the precipitate is isolated and this procedure is repeated

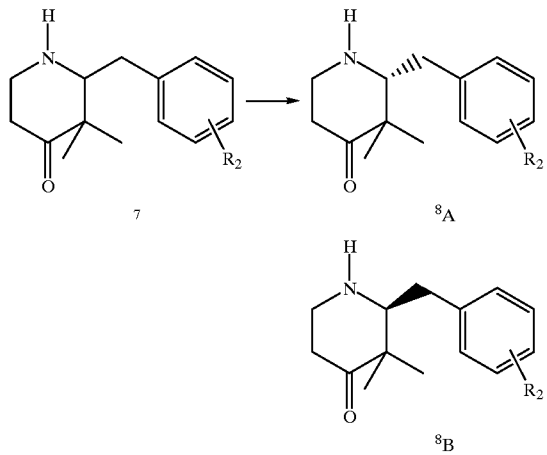

and f) the pure (+)-2-(3-methoxyphenyl)methyl-3,3-dimethyl-4-piperidonium hydrogen tartrate of type 8A ($R_2$=3-$OCH_3$) thus obtained is liberated from the enantiomerically pure acid addition salt and then subjected to a Wittig reaction in tetrahydrofuran with methyl triphenylphosphonium bromide in the presence of potassium tert.-butoxide at a temperature of 40° C., after the reaction is complete the mixture is combined with water and with dichloromethane, the aqueous phase is extracted exhaustively, the (+)-2-(3-methoxyphenyl)methyl-3,3-dimethyl-4-methylene-piperidine (9) is isolated and converted with hydrochloric acid into the (+)-2-(3-methoxyphenyl)methyl-3,3-dimethyl-4-methylene-piperidine hydrochloride of type 9 ($R_2$=3-$OCH_3$)

(9)

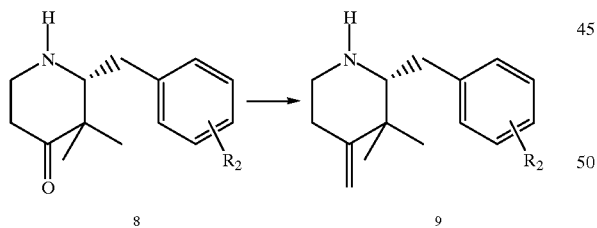

and g) the (3-methoxyphenyl)methyl-3,3-dimethyl-4-methylene-piperidine (9) ($R_2$=3-$OCH_3$) obtained from the Wittig reaction is liberated from its hydrochloride and the free base is dissolved in toluene and subjected with n-butylformate to a reaction of formylation at the piperidine nitrogen and the (+)-N-formyl-2-(3-methoxyphenyl)methyl-3,3-dimethyl-4-methylene-piperidine of type 10 ($R_2$=3-$OCH_3$) is isolated

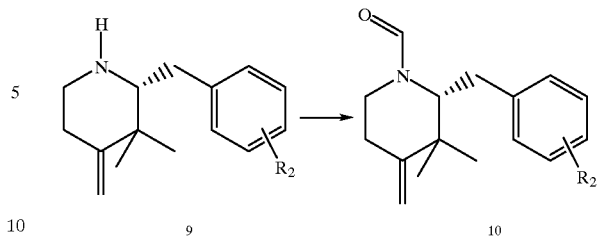

and h) the (+)-N-formyl-2-(3-methoxyphenyl)methyl-3,3-dimethyl-4-methylene-piperidine of type 10 ($R_2$=3-$OCH_3$) is dissolved in dichloromethane and reacted with aluminium(III)chloride and the (−)-2-formyl-3'-methoxy-5,9,9-trimethyl-6,7-benzomorphan of type 11 ($R_2$=3'-$CH_3O$) resulting from this reaction is isolated

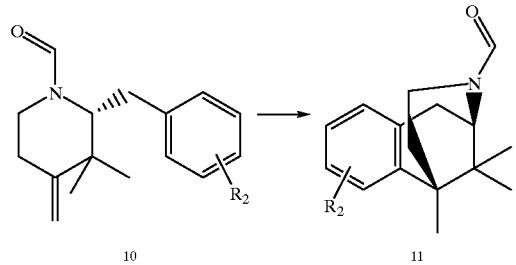

and i) the (−)-2-formyl-3'-methoxy-5,9,9-trimethyl-6,7-benzomorphan of type 11 ($R_2$=3'-$CH_3O$) resulting from the cyclisation is dissolved in n-propanol and reacted with concentrated hydrochloric acid and the (−)-3'-methoxy-5,9,9-trimethyl-6,7-benzomorphan of type 12 ($R_2$=3'-$CH_3O$) resulting from this reaction is converted with hydrochloric acid into the hydrochloride

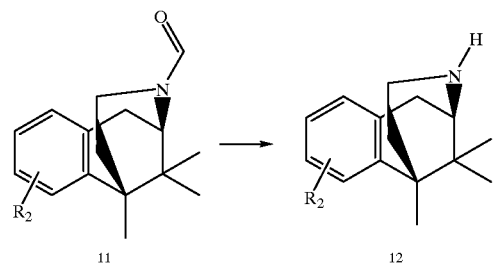

and j) after liberation of the free (−)-3'-methoxy-5,9,9-trimethyl-6,7-benzomorphan of type 12 ($R_2$=3'-$CH_3O$) from the hydrochloride, the 3'-methoxy function is converted with aqueous hydrobromic acid into a free hydroxy function under reflux conditions and the (−)-3'-hydroxy-5,9,9-trimethyl-6,7-benzomorphan of type 1 is converted with hydrobromic acid into the corresponding (−)-3'-hydroxy-5,9,9-trimethyl-6,7-benzomorphan-hydrobromide of general formula 13 ($R_2$=3'-OH) which corresponds to general formula 1.

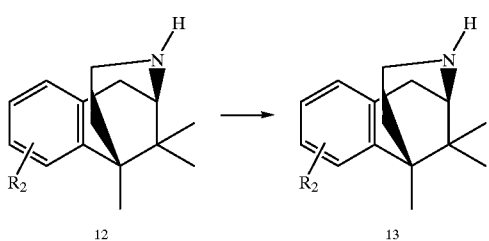

6. Process according to any one of claims 1 through 5, characterised in that, if $R_1$ denotes nitro, cyano, —$NH_2$, —$NH(C_1$–$C_8$-alkyl), —$N(C_1$–$C_8$-alkyl)$_2$ wherein the alkyl radicals may be the same or different, -NH-acyl-(($C_1$–$C_8$-alkyl), wherein acyl may also denote a benzoyl radical or an alkyl-carbonyl radical having a branched or unbranched lower alkyl radical having 1 to 6 carbon atom(s), wherein the alkyl radical may be substituted by one or more halogen atom(s) which may be the same or different, then, a compound of general formula 12, wherein $R_2$ denotes hydrogen, is processed by methods known per se from the state of the art to give a compound of general formula 13 which is functionalized correspondingly.

* * * * *